(12) United States Patent
Chen et al.

(10) Patent No.: US 7,560,599 B2
(45) Date of Patent: Jul. 14, 2009

(54) METHOD FOR PREPARING POLYMETHOXYMETHYLAL

(75) Inventors: Jing Chen, Lanzhou (CN); Zhonghua Tang, Lanzhou (CN); Chungu Xia, Lanzhou (CN); Xinzhi Zhang, Lanzhou (CN); Zhen Li, Lanzhou (CN)

(73) Assignee: Lanzhou Institute of Chemical Physics, Chinese Academy of Sciences, Lanzhou Gansu (CN)

( * ) Notice: Subject to any disclaimer, the term of this patent is extended or adjusted under 35 U.S.C. 154(b) by 0 days.

(21) Appl. No.: 12/180,594

(22) Filed: Jul. 28, 2008

(65) Prior Publication Data

US 2009/0036715 A1    Feb. 5, 2009

(30) Foreign Application Priority Data

Jul. 31, 2007   (CN) .................. 2007 1 0018474

(51) Int. Cl.
 *C07C 43/30*  (2006.01)
 *C07C 43/303* (2006.01)
(52) U.S. Cl. .................. 568/594; 568/613; 568/618

(58) Field of Classification Search ............... 568/594, 568/613, 618
See application file for complete search history.

(56) References Cited

U.S. PATENT DOCUMENTS 6,160,174 A    12/2000   Hagen et al.
6,265,528 B1   7/2001    Hagen et al.

FOREIGN PATENT DOCUMENTS

WO    WO 2006/045506 A1    5/2006

*Primary Examiner*—Sikarl A Witherspoon
(74) *Attorney, Agent, or Firm*—Scully, Scott, Murphy & Presser, P.C.

(57) ABSTRACT

This invention describes a method for preparing polymethoxymethylal. By this method, polymethoxymethylal is prepared by a catalytic reaction using methanol and trioxymethylene as reactants and using an ionic liquid as catalyst under a relatively moderate reaction condition. The catalyst of this invention has a high catalytic activity and a high conversion; the reaction process is simple, easy to be operated and has a strong controllability; the distribution of the products after reaction is superior and the utilization ratio of the raw materials is high.

11 Claims, No Drawings

METHOD FOR PREPARING POLYMETHOXYMETHYLAL

TECHNICAL FIELD

The present invention relates to a method for preparing polymethoxymethylal.

BACKGROUND ART

Recently, with the continual increment of the oil consumption and the improvement of the people's environmental consciousness, the demand on the oil consumption and smoke degree of the internal combustion engines using oil as an energy source is rigorous increasingly, and in order to improve oil quality and reduce the discharge of hazardous gases, a method of adding additives into the oil is relatively simple, economical and easy to be carried out effectively. The cetane number (CN) of diesel oil is an important index for scaling the performance of diesel oil. By increasing the cetane number, the discharge of the black smoke can be restrained effectively. Moreover, the self-oxygen feeding ability of the oxygen-containing additives has obvious effect during accelerating the combustion of oils. Polymethoxymethylal is a new clean oil additive and is an effective additive for improving the combustion of diesel oils, increasing the cetane number, reducing the discharge of carbon dioxide and NOx (nitrogen oxides), reducing the oil consumption, as well as reducing the smoke discharge. Polymethoxymethylal $(RO(CH_2O)_mR$, having a very high CN value and oxygen content (42-49% for the methyl series and 30-43% for the ethyl series)) can be added into diesel oil by 10%~20% and reduces the discharge of NOx and CO substantially. Due to their vapor pressure, boiling point and solubility in oils, the polymethoxymethylal ($DMM_{3-8}$) of $3 \leq m \leq 8$ is generally appropriate for oil addition.

$DMM_{3-8}$ is early obtained by using methanol, formaldehyde, poly formaldehyde or glycol formal as raw materials under the catalysis of sulfuric acid or hydrochloric acid. Recently, the research on synthesizing $DMM_{3-8}$ with catalysis of liquid acids in the representative of BASF Co. has obtained a certain development (WO 2006/045506 A1). The series products with m=1~10 were obtained by using sulfuric acid and trifluoromethylsulfonic acid as catalysts and using methanol, methylal, polyformaldehyde and trioxymethylene as raw materials. However, the catalysts are corrosive, the distribution of the products is not reasonable, and the conversion and the components available for oil additives are low, wherein, methylal is 33.5%, $DMM_2$ is 23.6%, $DMM_{3-11}$ is 28.3%, and the other m>11, wherein, the $DMM_{3-8}$ as the effective additive component is below 28.3%. A multiphase catalysis has been developed in the representative of BP Co. (U.S. Pat. Nos. 6,160,174, 62,655,284) and obtained polymethoxymethylal by a multistep process using methanol, formaldehyde, dimethyl ether and methylal as raw materials. Wherein, methylal is retained by 22.6%, $DMM_2$ is 12.42%, $DMM_{3-11}$ is only 11.6% and the other m>11, therefore, the breakthrough in key technology has not been achieved.

Up till now, due to the disadvantages of relatively low activity, rigorous reaction conditions, complex process and the like for $DMM_{3-8}$ synthesis catalysts, this technology has not been actually employed.

DISCLOSURE OF THE INVENTION

An object of this invention is to provide a method for preparing polymethoxymethylal by overcoming the disadvantages of relatively low activity, rigorous reaction conditions, complex process and the like existing in the prior art.

The present inventive concept is to catalytically synthesize polymethoxymethylal by using methanol and trioxymethylene as reactants and selecting an ionic liquid as catalyst under a relatively moderate reaction condition.

The reaction can be represented by the following scheme:

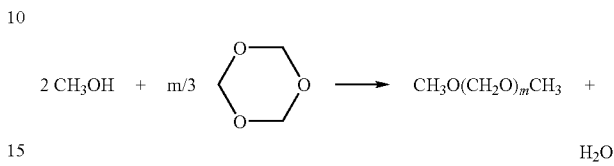

Wherein, m represents an integer of 1 to 11.

A method for preparing polymethoxymethylal, characterized in that: preparing polymethoxymethylal by a catalytic reaction using methanol and trioxymethylene as reactants and using an ionic liquid as catalyst with a controlled reaction temperature of 333~413K and a reaction pressure of 0.5 MPa~4 MPa; wherein, the cation portion of the ionic liquid is one selected from the group consisting of imidazolium cation, pyridinium cation, quaternary ammonium cation and quaternary phosphonium cation, and the anion portion is one selected from the group consisting of p-toluenesulfonate, trifluoromethylsulfonate, methylsulfonate, bisulfate and trifluoroacetate.

The structure formula of the imidazolium cation used in the invention is as follows:

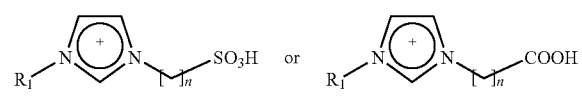

Wherein, n represents an integer of 0 to 15, $R_1$ represents an alkyl group or an aryl group.

The imidazolium cation generally selected is one selected from:

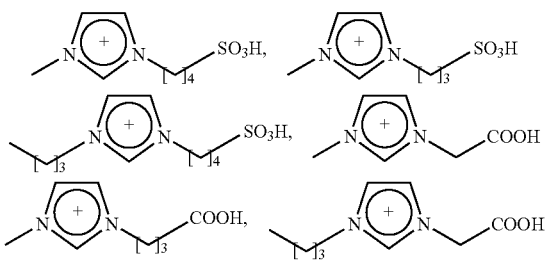

The structure formula of the pyridinium cation used in the invention is as follows:

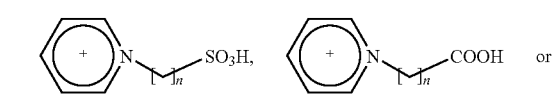

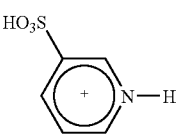

Wherein, n represents an integer of 0 to 15.

The pyridinium cation generally selected is one selected from:

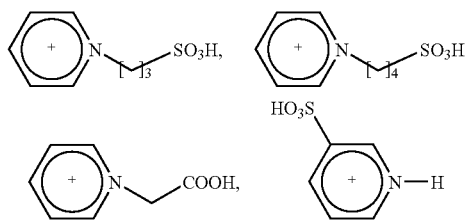

The structure formula of the quaternary ammonium cation used in the invention is as follows:

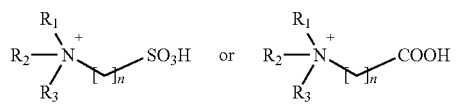

Wherein, n represents an integer of 0 to 15, $R_1$, $R_2$, and $R_3$ respectively represent a straight chain alkyl group with a carbon atom number of 1 to 4 or phenyl group.

The quaternary ammonium cation generally selected is one selected from:

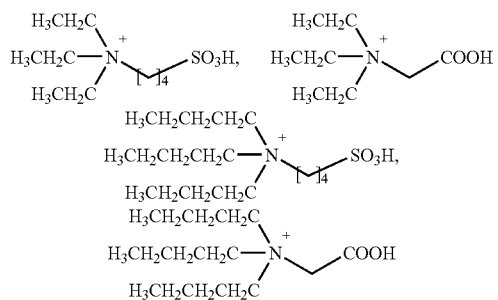

The structure formula of the quaternary phosphonium cation used in the invention is as follows:

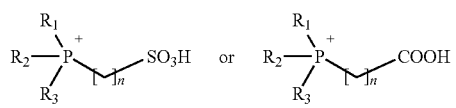

Wherein, n represents an integer of 0 to 15, $R_1$, $R_2$, and $R_3$ respectively represent a straight chain alkyl group with a carbon atom number of 1 to 4 or phenyl group.

The quaternary phosphonium cation generally selected is one selected from:

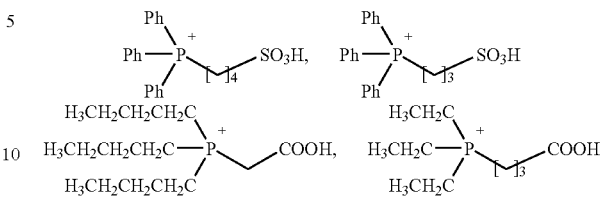

In the method of the invention, the molar ratio of trioxymethylene to methanol is 0.1~2.0.

In the method of the invention, the additive amount of the catalyst is 0.01~10 wt % of the total weight of all the reactants.

As compared with the prior art, this invention has the following advantages:

1, The amount of the catalyst is as low as 0.01~10 wt %; the catalyst has a high catalytic activity and a high conversion up to 90.3%.

2, The synthesis reaction can be carried out directly only with the two raw materials of methanol and trioxymethylene, and due to the characteristic of the ionic liquid, the reaction has a low corrosivity.

3, The reaction condition with a temperature of 333~413K and a pressure of 0.5 MPa~4 MPa is moderate. The reaction process is simple, easy to be operated and has a strong controllability.

4, The distribution of the products after reaction is superior, the utilization ratio of the raw materials is high, and the content of the effective diesel oil addition component $DMM_{3-8}$ can be up to 43.7%.

SPECIFIC MODES OF CARRYING OUT THIS INVENTION

The catalysts are represented as follows:

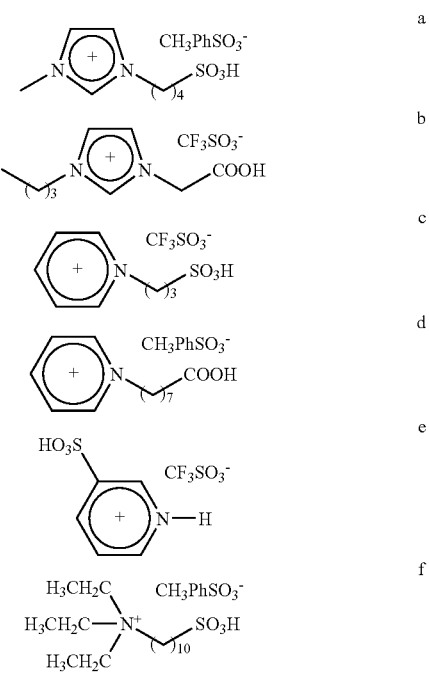

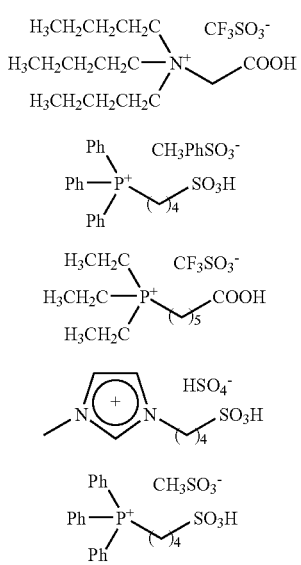

EXAMPLE 1

Into a 100 mL autoclave, 0.1203 g of catalyst a, 0.81 mL of methanol, 2.7 g of trioxymethylene were added in this order. A pressure of 2 MPa was achieved by introducing nitrogen gas and the mixture was heated to 353 K and stirred for 4 h. By gas chromatographic analysis, the conversion of trioxymethylene is 78.1% and the relative content of methylal is: m=1, 40.2%; m=2, 27.9%; m=3~8, 29.1%; m>8, 2.8%.

EXAMPLE 2

Example 2 is carried out in the same way as example 1. 0.2793 g of catalyst b, 0.81 mL of methanol, 2.7 g of trioxymethylene were added in this order. A pressure of 1 MPa was achieved by introducing nitrogen gas and the mixture was heated to 393 K and stirred for 5 h. By gas chromatographic analysis, the conversion of trioxymethylene is 79.6% and the relative content of methylal is: m=1, 39.7%; m=2, 21.6%; m=3~8, 30.3%; m>8, 8.4%.

EXAMPLE 3

The same as example 1, 0.0934 g of catalyst c, 2.43 mL of methanol, 2.7 g of trioxymethylene were added in this order. A pressure of 3 MPa was achieved by introducing nitrogen gas and the mixture was heated to 393 K and stirred for 6 h. By gas chromatographic analysis, the conversion of trioxymethylene is 82.1% and the relative content of methylal is: m=1, 30.7%; m=2, 28.1%; m=3~8, 39.7%; m>8, 1.5%.

EXAMPLE 4

The same as example 1, 0.0928 g of catalyst d, 1.62 mL of methanol, 2.7 g of trioxymethylene were added in this order. A pressure of 2 MPa was achieved by introducing nitrogen gas and the mixture was heated to 393 K and stirred for 1 h. By gas chromatographic analysis, the conversion of trioxymethylene is 88.7% and the relative content of methylal is: m=1, 57.3%; m=2, 31.5%; m=3~8, 11.2%; m>8, not detected.

EXAMPLE 5

The same as example 1, 0.0976 g of catalyst e, 2.02 mL of methanol, 2.7 g of trioxymethylene were added in this order. A pressure of 2 MPa was achieved by introducing nitrogen gas and the mixture was heated to 393 K and stirred for 4 h. By gas chromatographic analysis, the conversion of trioxymethylene is 78.9% and the relative content of methylal is: m=1, 39.5%; m=2, 26.3%; m=3~8, 30.1%; m>8, 4.1%.

EXAMPLE 6

The same as example 1, 0.5892 g of catalyst f, 3.24 mL of methanol, 5.4 g of trioxymethylene were added in this order. A pressure of 4 MPa was achieved by introducing nitrogen gas and the mixture was heated to 373 K and stirred for 4 h. By gas chromatographic analysis, the conversion of trioxymethylene is 88.5% and the relative content of methylal is: m=1, 42.5%; m=2, 30.1%; m=3~8, 26.4%; m>8, 1%.

EXAMPLE 7

The same as example 1, 0.4742 g of catalyst g, 3.24 mL of methanol, 5.4 g of trioxymethylene were added in this order. A pressure of 2 MPa was achieved by introducing nitrogen gas and the mixture was heated to 413 K and stirred for 3 h. By gas chromatographic analysis, the conversion of trioxymethylene is 86.7% and the relative content of methylal is: m=1, 27.9%; m=2, 29.4%; m=3~8, 41.5%; m>8, 1.2%.

EXAMPLE 8

The same as example 1, 0.9067 g of catalyst h, 16.2 mL of methanol, 27 g of trioxymethylene were added in this order. A pressure of 2 MPa was achieved by introducing nitrogen gas and the mixture was heated to 393 K and stirred for 4 h. By gas chromatographic analysis, the conversion of trioxymethylene is 90.3% and the relative content of methylal is: m=1, 25.4%; m=2, 28.7%; m=3~8, 42.6%; m>8, 3.3%.

EXAMPLE 9

The same as example 1, 0.8510 g of catalyst i, 16.2 mL of methanol, 27 g of trioxymethylene were added in this order. A pressure of 2 MPa was achieved by introducing nitrogen gas and the mixture was heated to 393 K and stirred for 4 h. By gas chromatographic analysis, the conversion of trioxymethylene is 81.2% and the relative content of methylal is: m=1, 21.7%; m=2, 34.3%; m=3~8, 39.2%; m>8, 4.8%.

EXAMPLE 10

The same as example 1, 0.8510 g of catalyst i, 48.6 mL of methanol, 27 g of trioxymethylene were added in this order. A pressure of 2 MPa was achieved by introducing nitrogen gas and the mixture was heated to 393 K and stirred for 4 h. By gas chromatographic analysis, the conversion of trioxymethylene is 82.4% and the relative content of methylal is: m=1, 52.3%; m=2, 24.2%; m=3~8, 23.5%; m>8, not detected.

EXAMPLE 11

The same as example 1, 1.0231 g of catalyst j, 48.6 mL of methanol, 27 g of trioxymethylene were added in this order. A pressure of 2 MPa was achieved by introducing nitrogen gas and the mixture was heated to 393 K and stirred for 2 h. By gas chromatographic analysis, the conversion of trioxymethylene is 82.1% and the relative content of methylal is: m=1, 24.7%; m=2, 33.5%; m=3~8, 39.7%; m>8, 2.1%.

EXAMPLE 12

The same as example 1, 3.60 g of catalyst k, 48.6 mL of methanol, 108 g of trioxymethylene were added in this order. A pressure of 2 MPa was achieved for 2 h. By gas chromatographic analysis, the conversion of trioxymethylene is 90.1% and the relative content of methylal is: m=1, 26.7%; m=2, 34.2%; m=3~8, 39.1%; m>8, not detected.

EXAMPLE 13

Using catalyst a, a methanol solution with a catalyst concentration of 10 wt % was prepared. In an autoclave with a polytetrafluoroethylene inner liner keeping at 393 K and a pressure of 3 MPa, the corrosivity of the solution was tested by a stainless steel hanging sheet. The corrosion ratio per year is 0.003 mm/a and shows that only a light corrosion occurred.

The invention claimed is:

1. A method for preparing polymethoxymethylal, characterized in that: preparing polymethoxymethylal by a catalytic reaction using methanol and trioxymethylene as reactants and using an ionic liquid as catalyst with a controlled reaction temperature of 333~413K and a reaction pressure of 0.5 MPa~4 MPa; wherein, the cation portion of the ionic liquid is one selected from the group consisting of imidazolium cation, pyridinium cation, quaternary ammonium cation and quaternary phosphonium cation, and the anion portion is one selected from the group consisting of p-toluenesulfonate, trifluoromethylsulfonate, methylsulfonate, bisulfate and trifluoroacetate.

2. The method according to claim 1, characterized in that the structure formula of the imidazolium cation is as follows:

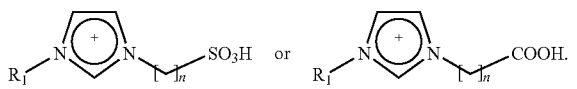

Wherein, n represents an integer of 0 to 15, and $R_1$ represents an alkyl group or an aryl group.

3. The method according to claim 2, characterized in that the imidazolium cation is one selected from:

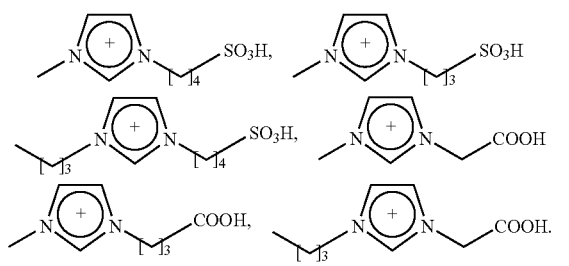

4. The method according to claim 1, characterized in that the structure formula of the pyridinium cation is as follows:

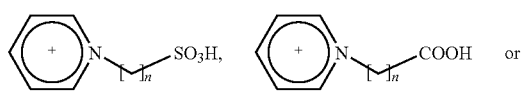

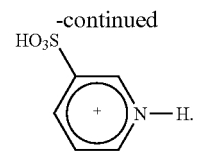

Wherein, n represents an integer of 0 to 15.

5. The method according to claim 4, characterized in that the pyridinium cation is one selected from:

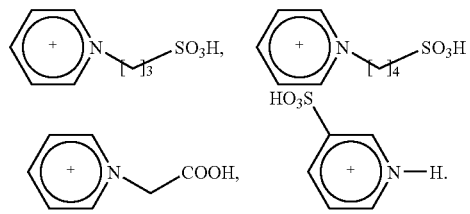

6. The method according to claim 1, characterized in that the structure formula of the quaternary ammonium cation is as follows:

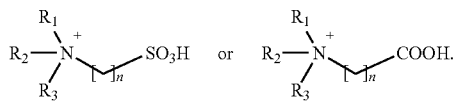

Wherein, n represents an integer of 0 to 15, $R_1$, $R_2$, and $R_3$ respectively represent a straight chain alkyl group with a carbon atom number of 1 to 4 or a phenyl group.

7. The method according to claim 6, characterized in that the quaternary ammonium cation is one selected from:

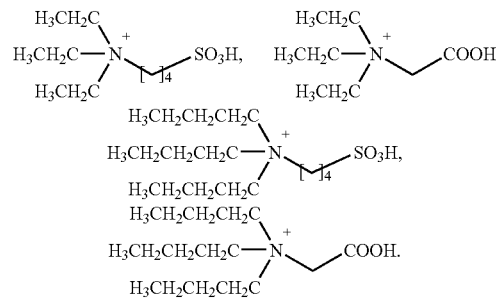

8. The method according to claim 1, characterized in that the structure formula of the quaternary phosphonium cation is as follows:

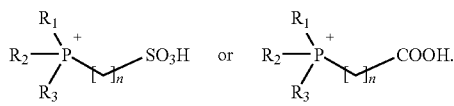

Wherein, n represents an integer of 0 to 15, $R_1$, $R_2$, and $R_3$ respectively represent a straight chain alkyl group with a carbon atom number of 1 to 4 or a phenyl group.

9. The method according to claim 8, characterized in that the quaternary phosphonium cation is one selected from:

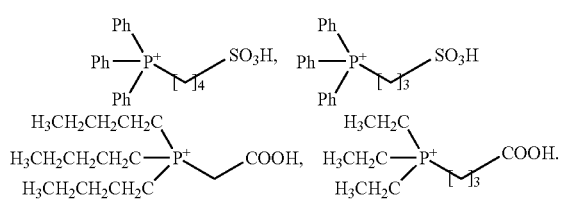
10. The method according to claim 1, characterized in that the molar ratio of trioxymethylene to methanol is 0.1~2.0.
11. The method according to claim 1, characterized in that the use amount of the catalyst is 0.01~10 wt % of the total weight of all the reactants.
* * * * *